United States Patent [19]

Farmar et al.

[11] Patent Number: 5,017,696

[45] Date of Patent: May 21, 1991

[54] ADVANCED GLYCOSYLATION END PRODUCTS AND ASSOCIATED METHODS

[75] Inventors: James G. Farmar; Peter Ulrich, both of New York; Anthony Cerami, Shelter Island, all of N.Y.

[73] Assignee: The Rockefeller University, New York, N.Y.

[21] Appl. No.: 453,935

[22] Filed: Dec. 20, 1989

Related U.S. Application Data

[63] Continuation of Ser. No. 97,856, Sep. 17, 1987, abandoned.

[51] Int. Cl.$^5$ .................... C07D 405/14; A61K 7/42; A61K 7/43; A61K 31/40
[52] U.S. Cl. .................. 536/18.7; 530/356; 530/362; 424/59; 422/61; 436/546; 436/504; 436/86; 436/543; 514/838; 514/885; 436/545
[58] Field of Search .............. 536/18.7, 356, 362

[56] References Cited

U.S. PATENT DOCUMENTS

| | | | |
|---|---|---|---|
| Re. 32,095 | 3/1986 | Wu et al. ............ | 536/18.7 |
| 4,306,577 | 12/1981 | Wu et al. ............ | 536/53 |
| 4,631,271 | 12/1986 | Mester et al. ....... | 536/18.7 |
| 4,665,192 | 5/1987 | Cerami ............... | 435/7 |
| 4,683,298 | 7/1987 | Yalpani .............. | 536/18.7 |
| 4,758,583 | 7/1988 | Cerami et al. ....... | 435/260 |
| 4,761,368 | 8/1988 | Cerami ............... | 435/7 |

OTHER PUBLICATIONS

Pongor et al., *Proc. Nat. Acad. Sci. U.S.A.*, 81, 2684 (1984) (Abstract) (101: 50317h Chem. Abstracts 1984).
NJOROGUE et al., *Carbohydrate Research*, 167, 211-220 (1987).
Farmar et al., *J. Organic Chemistry*, 53, 2346 (1988).
"Umsetzung Von Rebusierenden Zuchern Mit Alkylaminen Als Beitrag Zur Kenntnis Der Maillard-Reaktion," Ph.D. Thesis of Ulrich Kronig, Munich, 1974 (and partial translation).
"Kondensation Von Xylose Mit Methylammoniumacetat," Th. Severin and U. Kronig (and Translation).

*Primary Examiner*—Ronald W. Griffin
*Attorney, Agent, or Firm*—Klauber & Jackson

[57] ABSTRACT

New and useful chromophores have been isolated from the reaction mixture of proteins exposed to reducing sugars in the presence of sulfite over time. The chromophores are believed to be intermediates in nonenzymatic polypeptide glycosylation. The measurement of this chromophore makes possible both qualitative and quantitative assessment of the presence of nonenzymatic browning. Diagnostic and test kits are also disclosed.

10 Claims, 2 Drawing Sheets

ADVANCED GLYCOSYLATION END PRODUCTS AND ASSOCIATED METHODS

This invention was made with partial assistance from grants from the National Institutes of Health and the Brookdale Foundation.

This is a continuation of application Ser. No. 07/097,856, filed Sept. 17, 1987, now abandoned.

RELATED PUBLICATIONS

The Applicants are co-authors of the following article directed to the subject matter of the present invention: "Novel Pyrroles From Sulfite-Inhibited Maillard Reactions: Insight Into The Mechanism of Inhibition" (unpublished) James Farmar, Peter C. Ulrich, and Anthony Cerami, incorporated herein by reference.

BACKGROUND OF THE INVENTION

1. Field of the Invention

The present invention is directed generally to the reaction that occurs between glucose and proteins, and more specifically to the identification of a new group of compounds which form during nonenzymatic browning and whose existence became apparent by the studies of the inhibition of this reaction by sulfites.

2. Description of the Prior Art

The reaction between glucose and proteins has been known for some time. Its earliest manifestation was in the appearance of brown pigments during the cooking of food, which was identified by Maillard in 1912, who observed that glucose or other reducing sugars react with amino acids to form adducts that undergo a series of dehydrations and rearrangements to form stable brown pigments. Maillard, L. C. (1912) C. R. Acad. Sci., Vol. 154, pp. 66–68.

In the years that followed the initial discovery by Maillard, food chemists studied the hypothesized reaction in detail and determined that stored and heat treated foods undergo nonenzymatic browning as a result of the reaction between glucose and the polypeptide chain, and that the proteins are resultingly cross-linked and correspondingly exhibit decreased bioavailability. Finot, P. A. (1982) in *Modification of Proteins*, eds, Feeney, R. E. and Whitaker, J. R., American Chemical Society, Vol. 198, pp. 91–124, Washington, D.C. At this point, it was determined that the pigments responsible for the development of the brown color that develops as a result of protein glycosylation possessed characteristic spectral properties; however, the chemical structure of the pigments had not been specifically elucidated.

The reaction between reducing sugars and proteins discussed above was found in recent years to have its parallel in vivo. Thus, the nonenzymatic reaction between glucose and the free amino groups on proteins to form a stable 1-amino-1-deoxy-2-ketosyl adduct, known as the Amadori product, has been shown to occur with hemoglobin, wherein a rearrangement of the amino terminal of the beta-chain of hemoglobin by reaction with glucose, forms the adduct known as hemoglobin $A_{1c}$. This reaction was also found to occur with a variety of other body proteins, such as lens crystallins, collagen and nerve proteins. See, Bunn, H. F., Haney, D. N., Gabbay, K. H. and Gallop, P. H. (1975) Biochem. Biophys. Res. Comm. Vol. 67, pp. 103–109; Koenig, R. J., Blobstein, S. H. and Cerami, A. (1977) J. Biol. Chem. Vol. 252, pp. 2992–2997; Monnier, V. M. and Cerami, A. (1983) in *Maillard Reaction in Food and Nutrition*, ed. Waller, G. A., American Chemical Society, Vol. 215, pp. 431–448; and Monnier, V. M. and Cerami, A., (1982) Clinics in Endocrinology and Metabolism Vol. 11, pp. 431–452. Moreover, brown pigments with spectral and fluorescent properties similar to those of late-stage Maillard products have also been observed in vivo in association with several long-lived proteins, such as lens proteins and collagen from aged individuals. An age related linear increase in pigment was observed in human dura collagen between the ages of 0 to 90 years. See, Monnier, V. M. and Cerami, A. (1983) *Biochem. Biophys. Acta.*, Vol. 760, 97–103 (1983); and, Monnier, V. M., Kohn, R. R. and Cerami, A. "Accelerated Age-Related Browning of Human Collagen in Diabetes Mellitus", (1983) Proc. Nat. Acad. Sci. 81, 583–7. Interestingly, the aging of collagen can be mimicked in vitro by the crosslinking induced by glucose; and the capture of other proteins and the formation of adducts by collagen, also noted, is theorized to occur by a crosslinking reaction, and is believed to account for the observed accumulation of albumin and antibodies in kidney basement membrane. See, Brownlee, M., Pongor, S. and Cerami, A. (1983) *J. Exp. Med.*, 158, 1739–1744 (1983).

In general, little detailed information is available on the chemistry of the late-stage Maillard process, and it has been correspondingly difficult to determine the relation if any, that nonenzymatic browning may bear to the structural and functional changes in tissues that occurs during the aging process, and has likewise been observed to occur at an accelerated rate in individuals suffering from diabetes mellitus. Accordingly, a need therefore exists to identify to the extent possible, the structure and activity of the end products of advanced protein glycosylation, to aid in identifying the occurrence of advanced glycosylation, and to serve as an exploratory tool for the development and test of possible agents and corresponding treatments designed to retard or inhibit this form of protein aging.

2-Furoyl-4(5)-2(furanyl)-1H-imidazole has been isolated from the acid hydrolysates of browned proteins and is believed to be a cross-linker from the nonenzymatic browning of proteins, Pongor et al., *Prod. Natl. Acad. Sci. USA*, 81, 2684 (1984), and U.S. Pat. No. 4,665,192 (1987) and U.S.S.N. 885,967, filed July 15, 1986 and entitled "Methods and Agents for Measuring Protein Aging".

Methods of inhibiting the Maillard reaction in vivo using aminoguanidine are known, Brownlee et al., *Science*, 232, 1629 (1986), and U.S.S.N. 798,032, filed Nov. 14, 1985, and entitled "Method and Agents for Inhibiting Protein Aging". In the food industry, sulfites were found years ago to inhibit the Maillard reaction and are now commonly used in processed and stored foods. Recently, however, sulfites in food have been implicated in severe and even fatal reactions in some asthmatics. As a consequence, the sulfite treatment of fresh fruits and vegetables has recently been banned. The mechanism for the allergic reaction is not known. Due to the severity of the possible reaction, it is imperative for sulfite-allergic subjects to know when a foodstuff has been so-treated.

SUMMARY OF THE INVENTION

In accordance with the present invention, chromophores have been isolated and identified which are found to be present in sulfite-inhibited Maillard reactions. The compounds are adducts of an amino group and two molecules of reducing sugar. The compounds are isolated from a sulfite-containing reaction mixture of a reducing sugar and a compound with an amino group, and have the following structure:

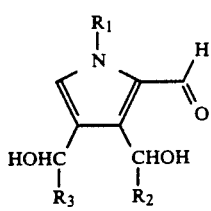

wherein $R_1$ is a des-amino residue of an amino-containing compound; $R_2$ is a glycosyl residue or hydrogen; and $R_3$ is a glycosyl residue.

The amino-containing compound of $R_1$, may be of substituted or unsubstituted nature. Typically, it is an amino acid, protein, or amino acid containing biopolymer which is usually naturally occurring, but which may also be synthetically produced.

The glycosyl residues of $R_2$ and $R_3$ are the two carbons which have been incorporated into the pyrrole ring structure. Suitable reducing sugars are those such as glucose, fructose, xylose, arabinose and maltose.

A preferred group of compounds of the present invention are those of the formulae Ia and Ib:

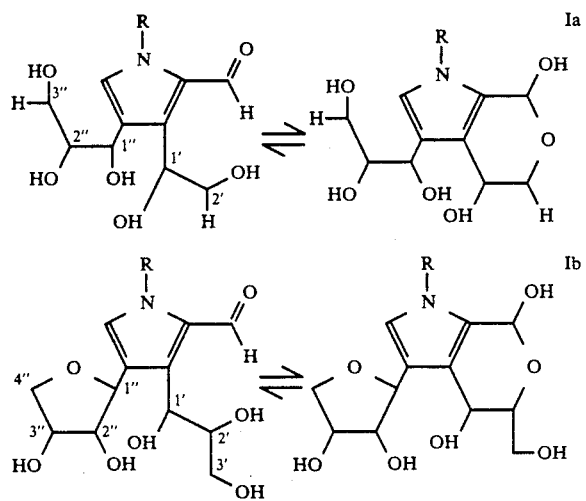

wherein R corresponds to $R_1$ of formula I as described above. Thus R is broadly the des-amino residue of an amino-containing compound, such compound selected from substituted and unsubstituted amino acids, proteins, and amino acid-containing biopolymers. More particularly, the amino-containing compound may be selected from the group consisting of 6-aminohexanoic acid, poly-L-lysine, methylamine, t-BOC-lysine, albumin, collagen, DNA, and mixtures thereof.

Thus, the compounds of this invention are 1-alkyl-2-formyl-3, 4-diglycosyl-pyrroles (abbreviated AFGPs, for convenience) where the reducing sugar is glucose.

Correspondingly, the present invention relates to the synthesis of these novel chromophores, by the nonenzymatic browning reaction of the named proteins with reducing sugars in the presence of sulfite.

The novel compounds of the present invention exist in a tautomeric state as the open chain aldehyde and two diastereomeric hemiacetals. They appear to arise from the reaction of the Amadori product of the amine-containing compound and a sugar derivative, 3-deoxy-glycosulose. Both of these types of compounds have been found in the sulfite-inhibited and sulfite-free non-enzymatic reaction.

These compounds structurally resemble pyrrolylcarbinols which are known to act as mono- and bis-alkylating agents by virtue of an alpha-hydroxyalkyl group attached to $C_3$ or $C_4$ of the pyrrole. Thus, AFGPs react similarly with nucleophiles such as an amino group of a nearby protein, a requirement for an intermediate involved in the in vivo crosslinking of proteins during non-enzymatic browning.

The appearance of these compounds in the presence of sulfite suggests that sulfite is responsible for the trapping of these intermediates which are believed to be naturally occurring intermediates in the Maillard process in vivo.

The present invention also relates to a method for measuring the presence of 1-alkyl-2-formyl-3,4-diglycosyl-pyrroles, and thus to a method for the quantitation of non-enzymatic browning in a protein material. Since the formation of AFGPs is accelerated in the presence of sulfite, quantitation in proteins may also indicate whether the protein had been exposed to sulfite, for example, during processing. More particularly, the presence of the compounds may be followed directly by the assay techniques discussed later on, through the use of an appropriately labeled quantity of the compound. Alternately, the compound can be used to raise binding partners or antibodies that could in turn, be labeled and introduced into a medium containing a protein under investigation to measure the quantity or location of the chromophore present in the protein sample.

Thus, both the chromophores of the present invention and any antibodies that may be raised therefrom, are capable of use in connection with various diagnostic techniques, including immunoassays, such as a radioimmunoassay, using for example, a chromophore labeled by either radioactive addition, reduction with sodium borohydride, or radioiodination.

In an immunoassay, a control quantity of the chromophore, its antibody, or the like may be prepared and labeled with an enzyme, a specific binding partner and/or a radioactive element, and may then be introduced into a sample of protein material. After the labeled chromophore or its binding partner(s) has had an opportunity to react with available protein material, the resulting mass may be examined by known detecting techniques, which may vary with the nature of the label attached.

In the instance where a radioactive label, such as the isotopes $^{14}C$, $^{131}I$, $^{3}H$, $^{125}I$ and $^{35}S$ are used, known currently available radionuclide detection procedures may be utilized. In the instance where the label is an enzyme, detection may be accomplished by any of the presently utilized colorimetric, spectrophotometric, fluorospectrophotometric or gasometric techniques known in the art.

The present invention includes an assay system which may be prepared in the form of a test kit for the quantitative analysis of the presence of nonenzymatic protein glycosylation products. The system or test kit may comprise a labeled component prepared by one of the radioactive an/or enzymatic techniques discussed herein, coupling a component of one of the advanced glycosylation end products, such as the present chromophore; and one or more additional immunochemical reagents, at least one of which is a free or immobilized ligand, capable either of binding with the labeled component, its binding partner, one of the components to be determined or their binding partner(s).

In conjunction with the investigative methods and materials identified herein, the invention may extend to potential methods of treatment to either retard or inhibit the glycosylation of proteins, by a procedure involving the examination of the protein sample for the presence of the chromophores, 1-alkyl-2-formyl-3,4-diglycosyl-pyrroles, in accordance with one of the methods specified earlier; followed by the development of a first binding partner or antibody to the chromophore, the subsequent development of a second binding partner or antibody specific to the first binding partner, and the administration of the latter binding partner either to the remainder of the protein mass in the instance of foodstuffs, or the area from which the protein sample was taken in the instance of living animal tissue or serum, in an effort to prevent the protein mass from entering a further stage of the Maillard process.

It is also contemplated that an AFGP may be used to stimulate the immune response of an animal. Macrophages have receptors for advanced glycosylation end-products (AGEs) which enable the body to recognize and remove AGEs. AFGPs may be able to stimulate macrophages to increase the activity of recognition and removal. In particular, phagocytic cells such as monocytes and macrophages are treated with a 1-alkyl-2-formyl-3,4-diglycosylpyrrole which causes the phagocytic cells to increase their activity of recognizing and removing macromolecules such as target proteins. Detailed methodology regarding such administration is as described in U.S.S.N. 907,747 filed Sept. 2, 1986 and entitled "Method and Agents for Removing Advanced Glycosylation Endproducts". Additionally, AFGPs may be utilized as immune adjuvants for poorly immunogenic antigens.

The identification of the chromophore of the present invention makes possible the continued investigation of the Maillard process and promotes efforts to identify other specific end products of advanced protein glycosylation. The chromophore and the various investigative methods associated with its isolation and identification will assist in elucidating the details of the chemical reactions that constitute late stage glycosylation, and will hopefully hold the key to identifying other specific agents that can serve to retard or inhibit the Maillard process and thereby extend the useful life of the protein. This development is particularly important as the proteins most acutely affected by the Maillard process, such as collagen, are present in substantial quantities in many of the important body tissues, and correspondingly exert a pronounced effect on the functioning of the body with the onset of advanced age. The condition of diabetes mellitus, with increased blood levels of glucose would be expected to have an even more deleterious effect by promoting the formation of Maillard products in the body.

The 1-alkyl-2-formyl-3,4-diglycosyl-pyrroles of the present invention will chemically cross-link with the amino group of various proteins. This reaction enables these 1-alkyl-2-formyl-3,4-diglycosyl-pyrroles to be utilized as cross-linking agents for proteins and to be further utilized in methods to quantitate said proteins by measuring the reactivity of proteins in a biological sample with a known amount of a 1-alkyl-2-formyl-3,4-diglycosyl-pyrrole.

An additional application of the present invention is to the science of food technology, as the chromophore and the assay procedures in which it is useful, may be employed to test for and identify the former or current presence of the possibly toxic sulfites in a foodstuff or other protein sample. Thus, various foodstuffs or other samples could be inspected by resorting to one of the assay procedures set forth above, to determine with quantitative exactitude, the onset and extent of protein aging in the presence of sulfites. Such accuracy is particularly possible in the instance where the present chromophore is incorporated into a radioimmunoassay system, such as one employing radioiodination or the introduction of a radioactive label by reduction of the chromophore with sodium borohydride.

Accordingly, it is a principal object of the present invention to identify the specific chromophore present in protein having undergone advanced nonenzymatic glycosylation.

It is a further object of the present invention to provide procedures for the isolation and identification of the chromophore as aforesaid on both an in vivo and in vitro basis.

It is a still further object of the present invention to provide methods for measurement of the chromophore as aforesaid which served to elucidate the stage of glycosylation of the protein sample under investigation.

It is a still further object of the present invention to provide methods for identifying other advanced glycosylation end products in protein samples subjected to late-stage glycosylation by assay procedures utilizing the chromophore identified herein.

It is a still further object of the present invention to provide methods for the measurement of the current or former presence of sulfite in a given protein sample.

It is a still further object of the present invention to provide a method of crosslinking proteins by reacting said proteins with a 1-alkyl-2-formyl-3,4-diglycosylpyrrole.

A still further object of the present invention is to measure antibodies to a 1-alkyl-2-formyl-3,4-diglycosyl-pyrrole in the body as a measure of allergy to sulfite.

Other objects and advantages will become apparent to those skilled in the art from a review of the ensuing description which proceeds with reference to the following illustrative drawings.

DETAILED DESCRIPTION

In its primary aspect, the present invention concerns the isolation and identification of chromophores which have been found to be present in proteins that have been incubated with a reducing sugar in the presence of sulfite. In particular, such proteins exhibit several physicochemical changes, including crosslinking. The chromophores which have been isolated and identified herein as 1-alkyl-2-formyl-3,4-diglycosyl-pyrroles, appear to represent intermediates believed to be involved in the Maillard process which are trapped by reaction in the presence of sulfites.

The compounds, 1-alkyl-2-formyl-3,4-diglycosyl-pyrroles, the structural formulae of which have been described earlier herein (referred to hereinafter for brevity as AFGPs), are a condensation product of two glucose molecules and one amino group which are produced in quantity by the nonenzymatic browning process occuring in the presence of sulfite.

Typically, an aqueous solution of the reducing sugar and the amino acid in a sodium phosphate buffer (pH 7.35, 0.5 M phosphate) in the presence of sulfite is incubated at 35-40° C. in the dark for 20-30 days in tightly closed tubes. The sulfite-containing solutions did not become brown, but had a chromophore with strong absorption maximum at 300 nm with only minor tailing into the visible region. In order to isolate the chromophore, the reaction mixture is diluted and added to a Dowex AG 1x4 (100-200 mesh) in acetate form in a column. Elution with water affords a fraction containing glucose and the Amadori product from the amino acid. Elution with acetic acid (100 mM) affords a fraction containing the desired compounds of this invention, 1-alkyl-2-formyl-3,4-diglycosyl-pyrroles, which strongly absorb at 300 nm. This eluate is adjusted to pH 9 with ammonia and lyophilized to provide the products as brown oils. Purification, using a Mono Q anion exchange column, yields the products as hygroscopic solids.

Figure 1:
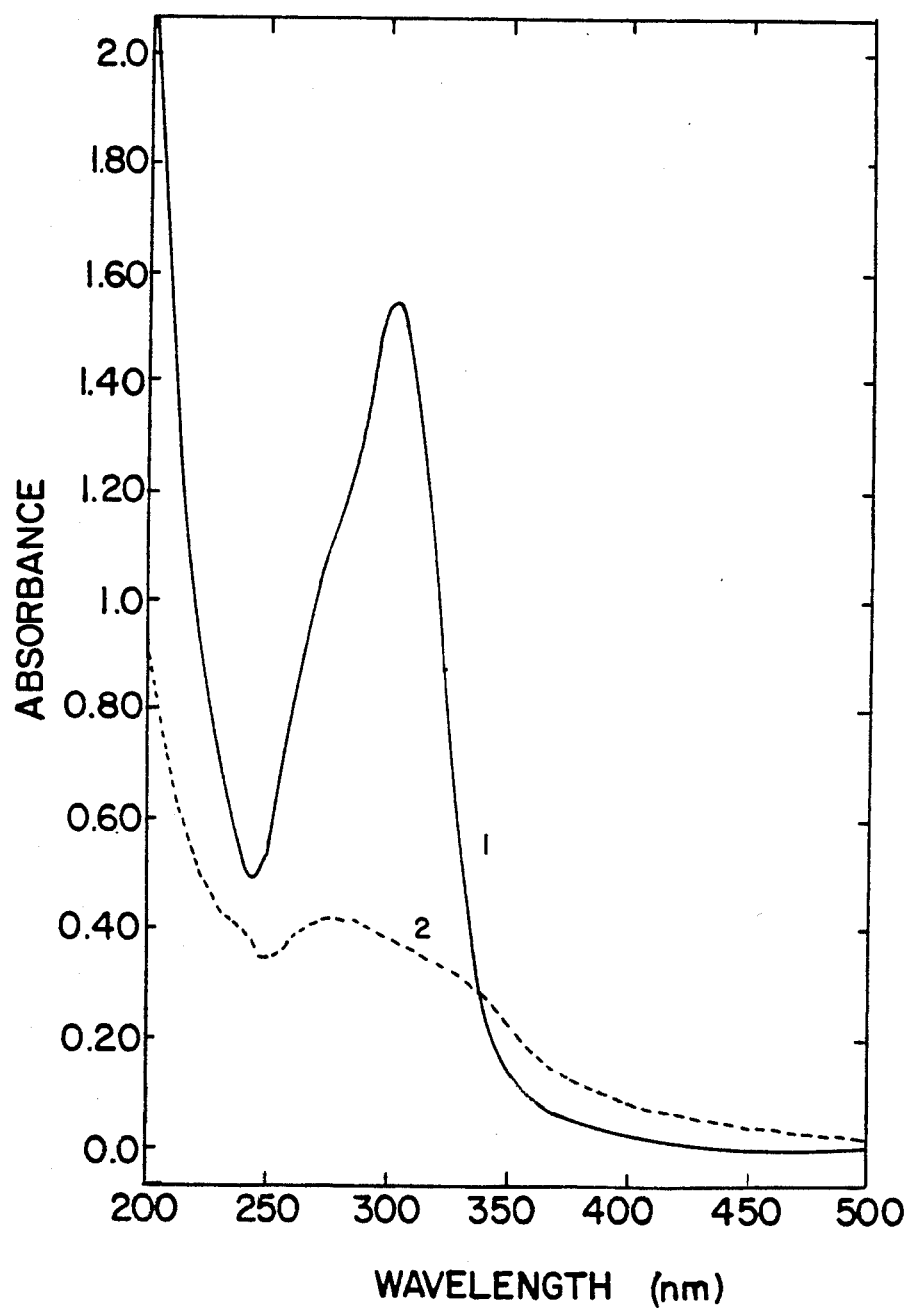
FIG. 1 is a graph depicting the increasing ultraviolet absorbance in the reaction of 6-aminohexanoic acid with glucose in sulfite-free and sulfite inhibited reactions.

The difference between reactions containing sulfite and those which are sulfite free can be observed in FIG. 1 which shows the absorptions of comparative reaction mixtures with (line 1) and without sulfite (line 2). This absorption peak at 300 nm can be utilized as an indicator of the reaction during the process of the present invention. It can be noted from FIG. 1 that a significantly greater amount of the 300 nm chromophore forms in the presence of sulfite than in the absence of sulfite. It can likewise be utilized diagnostically to indicate the likelihood of the former or current presence of sulfites in a given foodstuff.

Figure 2:
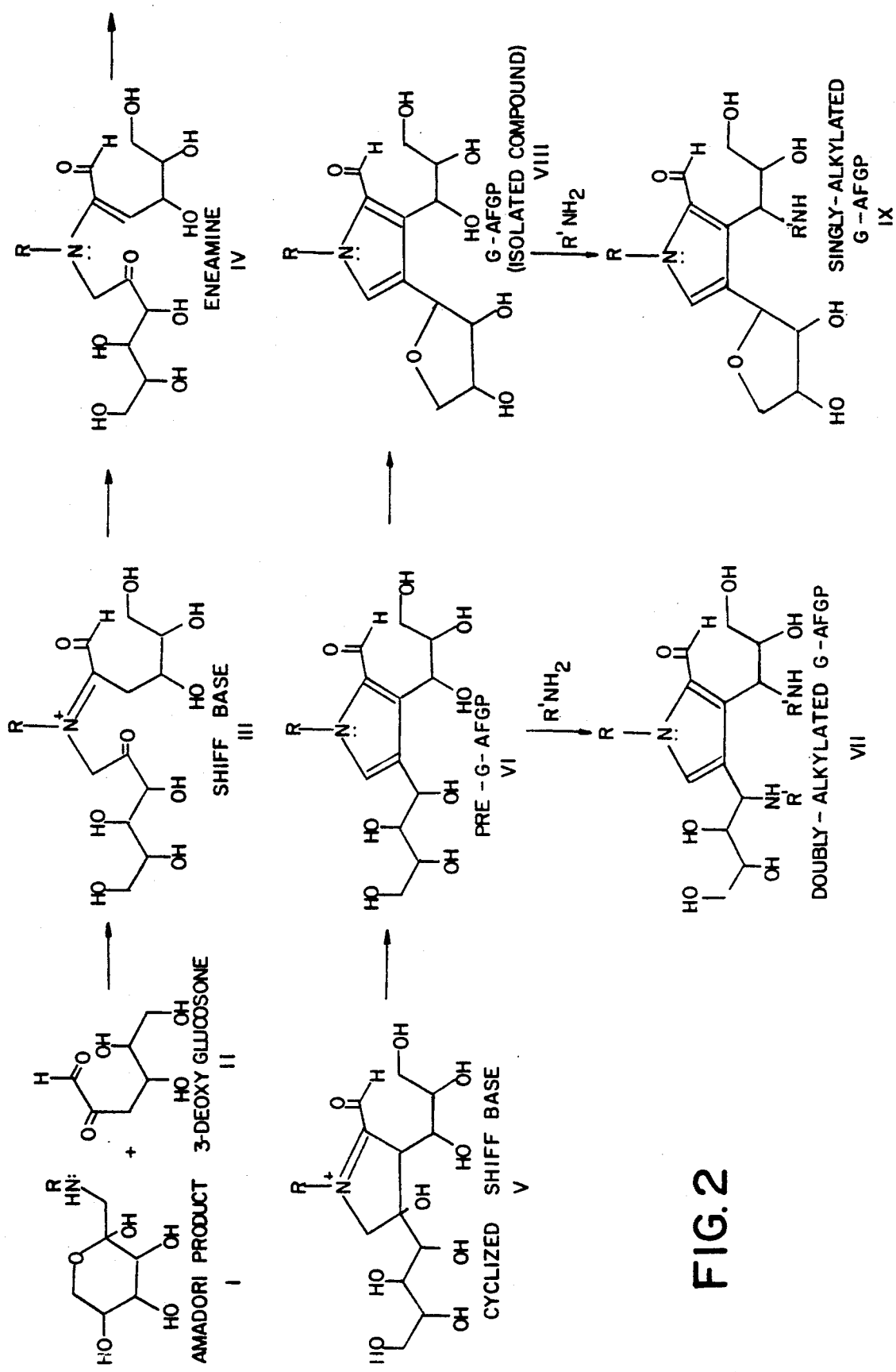
FIG. 2 is a diagram depicting possible reaction pathways between precursor compounds believed to form protein crosslinks similar in structure to the chromophore isolated in accordance with the present invention.

FIG. 2 shows the proposed pathway for formation of G-AFGPs. Amadori products (mono- and di-1-deoxy-2ketosyl amino acids) have been shown to form readily when (I) reducing aldoses are incubated with amino acids, and are considered to be the starting point of the Maillard reaction. 6-(1-deoxy-2-fructosyl)aminohexanoic acid can be isolated from a reaction mixture of glucose, 6-AHA and sulfite. The intermediate 3-deoxyglucosone (II) has been shown to arise from the decomposition of di-fructosyl amino acids, Anet, *Aust. J. Chem.* 13, 396 (1960). Nakano et al., *Tet. Letters,* 7, 737 (1966) have isolated an enamine (similar to IV) derived from an aminoketone and beta-keto-ester and have obtained a pyrrole from it in good yield. AFGPs are similar to a number of pyrrolylcarbinols studied by Mattocks et al., *Tox Lett.*, 1 (1983); *Chem-Biol Interactions,* 5, 227 (1972) and *J. Path.*, 100, 169 (1970) as the agents responsible for the liver and lung damage when plants containing pyrrolizidine alkaloids are ingested. These alpha-hydroxyl-pyrroles act as alkylating agents; their electrophilic site is a hydroxymethyl group attached to C3 or C4 of the pyrrole (Culvenor, *Aust J. Chem.,* 23, 1853 (1970)). Toxicity of compounds related to AFGPs (Mattocks, supra.) suggest that this may likewise be toxic and its formation responsible for deleterious effects of glucose.

In general, the reactions herein represent the products of reactions of 3-deoxyglycosuloses and Amadori products.

The chromophore of the invention may be used in a variety of investigative methods, in an effort to measure the extent of nonenzymatic glycosylation of a protein sample, as well as whether sulfites are or were present during the glycosylation processes. Both quantitative and qualitative determinations may be made, including the preparation of the chromophore with various radioactive or enzymatic labels and the introduction of the thus labeled chromophore into a protein mass to determine its state of glycosylation and chemical activity.

The chromophore may be labeled by a variety of techniques, depending upon the nature of the investigative procedure that is to be used. Thus, for example, a 1-alkyl-2-formyl-3,4-diglycosyl-pyrrole may be reacted with methoxyamine hydrochloride to form the methoxime derivative, or may be reduced with sodium borohydride. This preparation, illustrated herein in the chemical derivatization of the 1-alkyl-2-formyl-3,4-diglycosyl-pyrrole for mass spectrometry, can be utilized to place a radioactive label on the reduced form of the chromophore, such as by the reduction with a radioactive form of sodium borohydride, or by other methods known in the art. The resulting reduced derivative can then be employed in appropriate assay procedures.

Additionally, the labeled chromphore can be obtained by utilizing labeled reactants in the process for producing the AFGPs. Other labels commonly employed for such assay procedures may also be associated with the present chromophore and, for example, radioactive labels such as $^{14}C$, $^{131}I$, $^{3}H$, $^{125}I$ and $^{35}S$ may be appropriately introduced to the chromophore, or to carriers to which the chromophore is attached.

Other known labels comprise enzymes and fluorescent materials. Fluorescent materials are preferably considered in the instance where other non-fluorescent advanced glycosylation end products are isolated and are to be labeled for use in assay systems. Similarly, fluorescent labels may be used in the instance where the present chromophore has been employed to raise antibodies to itself, which antibodies are non-fluorescent.

A number of fluorescent materials are known and can be utilized as labels. These include, for example, fluorescein, rhodamine and auramine. A particular labeled conjugate that may be developed in accordance herewith is anti-rabbit antibody prepared in goats and conjugated with fluorescein through an isothiocyanate.

Enzyme labels are likewise useful, and can be detected by any of the presently utilized colorimetric, spectrophotometric, fluorospectrophotometric or gasometric techniques. The enzyme is conjugated to the selected chromophore by reaction with bridging or activating molecules such as carbodiimides, diisocyanates, glutaraldehyde and the like. Many enzymes which can be used in these procedures are known and can be utilized. The preferred are peroxidase, beta-glucuronidase, beta-D-glucosidase, beta-D-galactosidase, urease, glucose oxidase plus peroxidase and acid phosphatase. U.S. Pat. Nos. 3,654,090; 3,850,752; and 4,016,043 are referred to by way of example for their disclosure of alternate labeling material and methods.

The chromophore may be used to produce antibody(ies) to itself which can be produced and isolated by standard methods including the well known hybridoma techniques. The antibody(ies) can be used in another species as though they were antigen(s) to raise antibody(ies). Both types of antibody(ies) can be used to determine the amount and location of AFGPs in protein masses, whether in foodstuffs, or in the mammalian body. For convenience, the antibody(ies) to the chromophore will be referred to herein as $Ab_1$ and antibody(ies) raised in another species as $Ab_2$.

The degree of glycosylation in protein masses suspected of undergoing the same can be ascertained by the usual immunological procedures applicable to such determinations. A number of useful procedures are known. Three such procedures which are especially useful utilize either the chromophore labeled with a detectable label, antibody $AbI$ labeled with a detectable label, or antibody $Ab_2$ labeled with a detectable label. The procedures may be summarized by the following equations wherein the asterisk indicates that the particle is labeled, and "Ch" stands for chromophore:

A. $Ch^* + Ab_1 = Ch^*Ab_1$
B. $Ch + Ab_1^* = ChAb_1^*$
C. $Ch + Ab_1 + Ab_2^* = Ch\ Ab_1\ Ab_2^*$

The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure C, the "sandwich" procedure, is described in U.S. Pat. Nos. RE 31,006 and 4,016,043. Still other procedures are known such as the "double antibody", or "DASP" procedure.

In each instance, the chromophore substance forms complexes with one or more antibody(ies) or binding partners and one member of the complex is labeled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This is because $Ab_1$ raised in one mammalian species has been used in another species as an antigen to raise the antibody $Ab_2$. For example, $Ab_2$ may be raised in goats using $Ab_1$ as an antigen. $Ab_2$ therefore would be anti-rabbit antibody raised in goats. For purposes of this description and claims, $Ab_1$ will be referred to as a chromophore antibody and $Ab_2$ will be referred to an an antibody reactive with a chromophore antibody or, in the alternative, an "anti-antibody".

The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine and auramine. A particular detecting material is anti-rabbit antibody prepared in goats and conjugated with fluorescein through an isothiocyanate.

The chromophore or its binding partner(s) can also be labeled with a radioactive element or with an enzyme. The radioactive label can be detected by any of the currently available counting procedures. The preferred isotope may be selected from $^{14}C$, $^{131}I$, $^{3}H$, $^{125}I$ and $^{35}S$.

In a further embodiment of this invention, commercial test kits suitable for use either by a medical specialist or a food technologist may be prepared to determine the presence or absence of glycosylation end products in a suspected protein sample. In accordance with the testing techniques discussed above, one class of such kits will contain at least the labeled chromophore or its binding partner, an antibody specific thereto. Another which contain at least $Ab_1$ together with labeled $Ab_2$. Still another will contain at least $Ab_1$ and directions, of course, depending upon the method selected, e.g., "competitive", "sandwich", "DASP" and the like. The kits may also contain peripheral reagents such as buffers, stabilizers, etc.

Accordingly, a test kit may be prepared for the demonstration of AFGPs in protein masses, whether in food or in animals, comprising:

(a) a predetermined amount of at least one labeled immunochemically reactive component obtained by the direct or indirect attachment of glycosylation product, the present chromophore or a specific binding partner to either, to a detectable label;

(b) other reagents; and (c) directions for use of said kit.

More specifically, the diagnostic test kit may comprise:

(a) a known amount of the chromophore or the glycosylation product as described above (or a binding partner) generally bound to a solid phase to form a immunosorbent, or in the alternative, bound to a suitable tag, or plural such end products, etc. (or their binding partners) one of each;

(b) if necessary, other reagents; and (c) directions for use of said test kit.

In a further variation, the test kit may be prepared and used for the purposes stated above, which operates according to a predetermined protocol (e.g. "competitive", "sandwich", "double antibody", etc.), and comprises:

(a) a labeled component which has been obtained by coupling a component of one of said chromophore or said glycosylation products to be a detectable label;

(b) one or more additional immunochemical reagents of which at least one reagent is a ligand or an immobilized ligand, which ligand is selected from the group consisting of:

(i) a ligand capable of binding with the labeled component (a);

(ii) a ligand capable of binding with a binding partner of the labeled component (a);

(iii) a ligand capable of binding with at least one of the component(s) to be determined; and (iv) a ligand capable of binding with at least one of the binding partners of at least one of the component(s) to be determined; and (c) directions for the performance of a protocol for the detection and/or determination of one or more components of an immunochemical reaction between the advanced glycosylation end product and a specific binding partner thereto.

By example, a solid phase assay system or kit may comprise the solid substrate with either bound binding partner and labeled chromphore or bound chromophore and labeled binding partner. A supernatant containing the protein to be assayed is then placed in contact with the substrate and a competitive reaction between the labeled material and any unlabeled binding partner(s) in the sample will cause the release of a quantity of the former into the supernatant whereupon it can be precisely quantitatively identified. The foregoing explanation of a particular competitive assay system is presented herein for purposes of illustration only, in fulfillment of the duty to present an enabling disclosure of the invention. It is to be understood that the present invention contemplates a variety of diagnostic protocols within its spirit and scope.

As discussed earlier, the present invention includes potential methods for treating proteins undergoing glycosylation in an effort to retard if not totally inhibit the progress of the Maillard process. The method comprises the development of anti-antibody to the chromophore or to other isolated glycosylation products, that when administered to the glycosylating protein mass, serves by its structure and reactivity, to block rather than facilitate the continued glycosylation of the protein.

For example, an anti-antibody or second binding partner to a first binding partner to 1-alkyl-2-formyl-3,4-diglycosyl-pyrrole might be raised as in the practice of one of the earlier described assay procedures, which does not cause the proteins to crosslink. In this way, the administration of this non-crosslinking binding partner would block the final insolubilization and hardening of the protein and might thereby prolong its vitality and usefulness, whether in foodstuffs or in animal tissues. Administration of anti-antibody or second binding partner may form an immune complex activating the animal's earance system to remove said immune complex and associated AGES so that it can later be replaced. The foregoing scenario is naturally illustrative of a course of action that suggests itself as an outgrowth of the findings as to the aging process disclosed presently herein. Additionally, the AFGPs of this invention can be utilized as adjuvants due to their cross-linking potential with antigens and also as macrophage stimulants to activate the macrophage to effect removal of AGEs. When an AFGP is utilized as an adjuvant it is reacted or cross-linked with an antigen that is "weak". The addition of AFGP to the antigen produces an antigen which produces a strong reaction due to the presence of the AFGP portion, thus increasing the immunogenicity of the original antigen. The invention is not limited to this methodology, but rather encompasses it within its scope.

As noted earlier, phagocytic cells are capable of recognizing and removing abnormal macromolecules by means of receptors on their surfaces which recognize specific chemical structures and bind to them. Once the abnormal macromolecule is recognized in this way, the phagocytic cell may internalize the macromolecule or particle containing the abnormal macromolecule and may then degrade it. In some instances, the phagocytic cell may in addition secrete enzymes and other factors to help degrade the molecule or particle extracellularly if it cannot be internalilzed. After the damaged protein is removed, new growth of normal tissue can ensue, and normal function of the affected area may resume.

Phagocytic cells in the body comprise numerous types of white blood cells. One type of white blood cell, the monocyte, is produced in the bone marrow, and circulates briefly in the blood and thereafter enters the tissues where it becomes a macrophage. Exposure of the phagocytic cell either as a monocyte or a macrophage, to certain molecules can regulate the appearance on the surface of the cell of receptors for these molecules.

Thus, the present invention is predicated on the discovery that the phagocytic cells including monocytes and macrophages can be modified by exposure to stimulator compounds that potentiate the capability of these cells with respect to their recognition and affinity for, and capability to degrade advanced glycosylation endproducts. In particular, the exposure of these cells to certain stimulator compounds has been found to increase the number of receptors developed on these cells and to thereby increase the capacity and efficiency of these cells with respect to the recognition and degradation of advanced glycosylation endproducts. The 1-alkyl-2-formyl-3,4-diglycosyl-pyrroles of the present invention can function as stimulator compounds.

Accordingly, the method of the present invention generally comprises exposing the animal body to stimulator compounds, which cause the body, and its phagocytic cells in particular to become activated and to increase its recognition and removal of target macromolecules that have undergone advanced glycosylation.

The stimulator compounds useful in the present invention comprise the 1-alkyl-2-formyl-3,4-diglycosyl-pyrroles which may be employed alone or bound to a carrier.

The stimulator compounds can be bound to a carrier protein such as the protein albumin.

The carrier may be selected from the group consisting of carbohydrates, proteins, synthetic polypeptides, lipids, bio-compatible natural and synthetic resins, antigens and mixtures thereof.

As used herein, the term "antigen" includes various invasive stimuli that may comprise or cause the onset of pathology or other organic disability, such as protein and lipid fragments, bacteria, viruses and/or other organisms of similar origin and effect.

Additionally, all method aspects of the present invention can be utilized to detect the 1-alkyl-2-formyl-3,4diglycosyl pyrroles formed in an advanced protein glycosylation in the absence of sulfites. These AGFPs may be formed in the absence of sulfite as intermediates and their presence can be detected even without the presence of sulfite to trap them since, as noted previously, the chemical reactants which react to form AFGPs have been identified in nonenzymatic browning reactions in the absence of sulfite. The quantification can be used to determine the stage and amount of advanced protein glycosylation that has occurred.

An additional and related utility of the compounds involves their usage to detect the presence of the sulfite allergy in humans. This can be accomplished by testing the serum of a patient for the presence of antibodies to AFGPs (1-alkyl-2-formyl-3,4-diglycosylpyrroles). Since an allergic reaction may be the result of sensitization of an individual to AGFPs formed in the presence of sulfites, the characteristic antibodies will be present in the allergic individual's serum.

The 1-alkyl-2-formyl-3,4-diglycosyl-pyrroles of the present invention possess an aldehyde functional group which will reversibly cross-link with the amino group of various proteins. A non-reversible alkylation will occur via the alpha-hydroxymethyl-pyrrole carbon (FIG. 2, compounds VII and IX). This reaction can thus be utilized to provide such cross-linked protein products. These products which thus chemically incorporate the 1-alkyl-2-formyl-3,4-dyglycosyl-pyrroles and the change in the spectral properties can therefore be utilized to facilitate attachment of AFGP to proteins for the various uses described herein in and to link together two similar or dissimilar proteins for various purposes.

Additionally, this cross-linking reaction can be the basis of a therapy where it is desired to prevent or inhibit the particular protein from further reaction in a given system. The cross-linking with a 1-alkyl-2-formyl- 3,4-dyglycosyl-pyrrole thus prevents the protein from completing its normal or pathological reaction.

The 1-alkyl-2-formyl-3,4-diglycosyl-pyrroles of the present invention can also be utilized to quantitate the amount of protein in a biological sample. The biological sample is reacted with a known amount of the 1-alkyl-2-formyl-3,4-diglycosyl-pyrrole and then the amount of reaction is determined by measurement of the unreacted 1-alkyl-2-formyl-3,4-diglycosyl-pyrrole present in the contemplated reaction mixture.

A further use of the compounds of the present invention involves their use as sunscreens in view of their strong absorbance at 300 nm. As absorbers of this range of light, they block the most detrimental of the "burning" rays of natural sunlight. In their use as sunscreens, the compounds are typically formulated into lotions, ointments, creams and sprays utilizing known conventional vehicles for such use. Typically, the 1-alkyl-2-formyl-3,4-diglycosyl-pyrroles will be formulated so as to constitute 0.5% to 10 % by weight of the sunscreen composition, the remaining percentage being a compatible non-toxic, dermatologically acceptable vehicle.

Similarly, AFGPs can be incorporated into a formulation for a dermatological product where it is desired to add a brown coloration or "tan" to the skin without sun exposure. The AFGP in the formulation will react with the skin proteins and form brown pigments. Such a composition will be formulated so as to contain 0.5 to 10% by weight of the AFGP in a compatible, non-toxic dermatologically acceptable vehicle.

As mentioned earlier, the isolation and identification of the chromophore of the present invention involved the performance of a series of procedures upon representative proteins. The specific procedures and materials that were used in the preparation of the proteins, and the isolation and analysis of the chromophore that followed, are set forth below in the following illustrative examples.

EXAMPLE I

Aqueous solutions of glucose or xylose (2.78M) and 6-aminohexanoic acid (6-AHA) (0.382 M) in sodium phosphate buffer (ph 7.35, 0.5 M PO₄) in the presence or absence of sodium sulfite (0.2 M) are incubated at 37° C. in the dark for 26 days in tightly closed tubes; aliquots are withdrawn periodically to follow the reaction.

Visually and spectrophotometrically, the difference in the sulfite-containing reaction mixtures is striking. (See FIG. 1.) The sulfite-containing reactions do not become brown but have a chromophore with a strong absorption maximum at 300 nm with only minor tailing into the visible region. The sugar, amino acid, sulfite, and buffer are all required for generation of the 300 nm chromophore. The 300 nm chromophore is also produced when 6-AHA is replaced with methylamine, alpha-t-BOC-lysine, or poly-L-lysine (PLL). When xylose is substituted for glucose, the 300 nm chromophore is produced more rapidly.

In order to isolate the 300 nm chromphore, the sulfite-containing reaction mixture of glucose and 6-AHA is diluted and added to a column containing 40 g of Dowex AG 1×4 (100-200 mesh) in acetate form. Elution with water (1 L) gives a fraction containing glucose and the Amadori product from 6-AHA (See FIG. 2). After 400 ml of 100 mM acetic acid, material strongly absorbing at 300 nm eluted. The later eluate is adjusted to pH 9 with ammonia and lyophilized to yield 380 mg of a viscous, brown oil. A portion (55 mg) of this material is purified by chromatography on a Mono Q anion exhange column (FPLC, Pharmacia) using a thirty minute, linear gradient from 0–50 mM ammonium acetate in 5% methanol. The major chromophore eluted at twenty minutes to yield a hygroscopic amorphous dull yellow solid (21 mg, 38%). This material is acid sensitive; only 50% of the material was recovered when the spectroscopically pure compound was rechromatographed. A 300 nm-absorbing xylose adduct was isolated similarly.

The 1-alkyl-2-formyl-3,4-diglycosyl-pyrrole derived from glucose and 6-aminohexanoic acid is named glucose-derived-1-(5-carboxy-n-pentyl)-2-formyl-3,4 diglycosyl-pyrrole (G-AFGP) and the 1-alkyl-2-formyl-3,4-diglycosyl-pyrrole derived from xylose and 6-aminohexanoic acid is designated xylose-derived-1-(5-carboxy-n-pentyl)-2-formyl-3,4-diglycosyl-pyrrole (X-AFGP).

The failure of the products to bind to acidic ion exchange resins and the tendency of the adducts to form pink or red coloration in acid suggests that the nitrogen of the amino component was bound in the form of a pyrrole ring. When $NaHSO_3$ is added, the absorbance at 300 nm is greatly reduced. Addition of base to break up the bisulfite addition complex returns the 300 nm absorbance. $NaBH_4$ reduction also permanently removes the absorbance and indicates that the chromophore contained a conjugated aldehyde.

Ehrlich's reagent gives a purple color (594 and 504 nm), characteristic of a pyrrole with an electron withdrawing group. The 2,4-dinitrophenylhydrazone (2,4-DNP) of G-AFGP has properties similar to known N-alkyl-pyrrole-carboxaldehyde-2,4-DNP's ($\lambda$=416 nm, $\epsilon$ 17,500; 310 nm, $\epsilon$6550; 263 nm, $\epsilon$8700).

The infrared spectrum of G-AFGP showed hydroxyl groups (3400–3100, 1100, and 1040 $cm^{-1}$), a conjugated aldehyde (2870 and 1645 $cm^{-1}$), and carboxylic acid salt (1710 $cm^{-1}$). The peracetylated derivative has a strong ester band (1745 $cm^{-1}$) and conjugated aldehyde absorptions (2860 and 1660 $cm^{-1}$).

The UV/visible spectrum consists of a single absorbance at 300 nm (in $H_2O$, $\epsilon$8800) which was consistent with that of a 2-formylpyrrole.

The $^{13}C$ NMR spectrum of the glucose adduct has more than the expected number of resonances, indicating at least two components. The alkyl carbons of the hexanoate moiety clearly appears as five upfield resonances. The signals between 62 and 77 ppm are consistant with $R_3COH$ carbons. The downfield limit of the aromatic region (116–136 ppm) make both a pyridine and furan ring unlikely, but are consistent with a pyrrole. The carbonyl region (178.8, 181.2, and 181.8 ppm) can be explained by a carboxylic acid and at least one strongly shielded carbonyl (as in an electron-rich aromatic aldehyde).

Proton NMR in $D_2O$ (Table 1) reveals the presence of the expected hexanoic acid moiety methylenes and methines characteristic of polyhydroxylic side chains, and two major downfield singlets characteristic of an aromatic resonance (7.35 $\delta$) and an aldehyde (9.74$\delta$). There are additional minor signals in this region (6.00 $\delta$ (s) and 6.19 $\delta$(s); 6.85 $\delta$(m)) which are not removed or altered after repeated purifications. The peak integrations suggested that the compound exists primarily in the form of an aromatic aldehyde in $D_2O$, but that anomeric internal hemiacetal tautomers were also present, to the extent of 25–30% in the glucose adduct and 10–15% in the xylose adduct. These tautomers would have acetal methine resonances at ca. 6 δ, and upfield-shifted aromatic resonances at ca. 6.9 δ.

In the case of the xylose adduct, interpretation of the carbohydrate-like portion of the spectrum was very straightforward, as all resonances are fully resolved and coupling patterns are consistent with a 1,2-dihydroxyethyl group and a 1,2,3-trihydroxypropyl group attached to an aromatic ring. Based on the tetra-substitute pyrrole aldehyde fragment, the hexanoic acid side chain, and mechanistic constraints dictated by the starting materials, structures Ia ($R=CH_2CH_2CH_2CH_2CH_2COOH$) above have been assigned and are those of the xylose adduct, named xylose-derived-1-(5-carboxypentyl)-2-formyl-3,4-diglycosyl-pyrrole (X-AFGP). The parent ion (M, Table 2), determined by 252Cf Fission Fragment-Induced Ionization Mass Spectrometry (FFII-MS), is also consistent with this structure.

The $^1$H NMR spectrum of the glucose adduct is more complicated than expected for a 1,2,3-trihydroxypropyl group and a 1,2,3,4-tetrahydroxybutyl group. The glucose adduct needed more extensive spectrometric analysis and various derivatization procedures in order to clarify its nature.

The parent ion (M), determined by FFII-MS, is deduced to be 401 which Fast Atom Bombardment MS with LiCl supported. Exact Mass Electron Impact MS (EI-MS) of the peracetylated adduct suggests a molecular formula of $C_{26}H_{33}NO_{12}$.

EI-MS of the per-trimethylsilylated adduct and of the per-d9-trimethyl-silylated adduct demonstrates the presence of six trimethysilylation sites. Taken with the data from the peracetylated derivative, it can be concluded that G-AFGP contains five hydroxyl groups and one carboxyl group. More importantly, a molecular formula of $C_{18}H_{27}NO_9$ is found, which corresponds to loss of one water molecule.

Finally, FFI-MS of the BH4-reduced G-AFGP demonstrates the presence of one carbonyl which is also supported by incorporation of only one molecule of 2,4-dinitrophenylhydrazine in the nonreduced molecule.

With extensive IH NMR decoupling, 2D COSY[19] data, and comparison with the spectra of X-AFGP and erythrose, the structures of Ib are assigned to G-AFGP. This structure very likely is derived by the attack of C1 of the 1,2,3,4-tetrahydroxybutyl group by the terminal hydroxyl group to form the cyclic ether. A similar reaction for X-AFGP is unlikely because of the difficulty of forming a four-membered ring.

TABLE 1

| Sample | δ | Multiplicity & Coupling Constants | # H's | Assignment |
|---|---|---|---|---|
| X-AFGP | 1.23 | m | 2H | γ-$CH_2$ |
| in | 1.53 | m | 2H | δ-$CH_2$ |
| $D_2O$ | 1.77 | m | 2H | β-CH2 |
| | 2.16 | t, j = 7.4 Hz | 2H | α$CH_2$ |
| | 3.44 | dd, j = 6.9, 11.8 Hz | 1H | 3''-$CH_2$ |
| | 3.57 | dd, j = 3.5, 11.8 Hz | 1H | 3''-$CH_2$ |
| | 3.71 | dd, J = 4.7, 11.7 Hz | 1H | 2'-$CH_2$ |
| | 3.79 | dd, J = 7.6, 11.7 Hz | 1H | 2'-$CH_2$ |
| | 3.87 | dt, J = 3.5, 6.8 Hz | 1H | 2'-$CH_2$ |
| | 3.87 | dt, J = 3.5, 6.8 Hz | 1H | 2''CH |
| | 4.31 | br t, J = 6.8 Hz | 2H | δ-$CH_2$ |
| | 4.65 | br s | 1H | 1''-CH |
| | 5.18 | dd, J = 4.7, 7.6 Hz | 1H | 1'-$CH_2$ |
| | 7.30 | s | 1H | H-5 |
| | 9.74 | s | 1H | formyl |
| Toutomers (lb. r = H) | | | | |
| | 6.03 | s | | acetal methine |
| | 6.82 | m | | H-5 |
| in | 4.57 | d, J = 5.0 Hz | 1H | 1''-CH |
| $d_6$-DMSO | 4.93 | dd, J = 4.9, 6.7 Hz | 1H | 1'-CH |
| G-AFGP | 1.25 | t, J = 7.2 Hz. | 2H | γ-$CH_2$ |
| in | 1.55 | br m | 2H | δ-$CH_2$ |
| $D_2O$ | 1.77 | br m | 2H | β-$CH_2$ |
| | 2.35 | br t, J = 7.2 Hz | 2H | α-$CH_2$ |
| | 3.41 | dd, J 32 6.5, 11.9 Hz | 0.65H | 3'-$CH_2$ |
| | 3.50 | dd, J = 3.7, 11.8 Hz | 0.65H | 3'-$CH_2$ |
| | 3.62 | dd, J = 6.5, 11.8 Hz | 0.70H | 3'-$CH_2$ |
| | 3.79 m, J = 10.1, 12.0 Hz | | 2H | 4''-CH-hd 2 |
| | 3.87 | | | |
| | 4.30 | br m | 3H | δ-$CH_2$ & 2''-CH |
| | 4.39 | br m | 1H | 3''-$CH_2$ |
| | 4.87 | d, J = 8.2 Hz | 0.5H | 1''-CH |
| | 4.89 | d, J = 8.0 Hz | 0.5H | 1''-CH |
| | 5.04 | d, J = 7.0 Hz | 0.5H | 1'-CH |
| | 5.05 | d, J = 7.4 Hz | 0.5H | 1''-CH |
| | 7.35 | d, J = 3.5 Hz | 1H | H-5 |
| | 9.74 | d, J = 3.8 Hz | 1H | formyl |
| Tautomers (2b, R = $CH_2OH$) | | | | |
| | 6.00+ | | | acetal |
| | 6.19 | | | methine |
| | 6.85 | m | | H-5 |

TABLE 2

| Compound | Method | Ion (m/z) | Interpretation |
|---|---|---|---|
| | | MASS SPECTROSCOPY OF AFGPs | |
| X-AFGP | FF-11 (+) | 404 | $(M + 2Ha - H)^+$ |
| | | 382 | $(M + Na)^+$ |
| | (−) | 380 | $(M + Na - 2H)^-$ |
| G-AFGP | Cl | 384 | $(M + H - H_2O)^+$ |
| | | 366 | $(M + H - 2 H_2O)^+$ |
| | | 296 | $(M + H - H_2O - CO - (HO)CH=CH(OH))^+$ |
| | FAB (Li) | 408 | $(M + Li)^{30}$ |
| | | 390 | $(M + Li - H_2O)^+$ |
| | FF-11 (+) | 424 | $(M + Na)^+$ |
| | | 396 | $(M + Na - CO)^+$ |
| G-AFGP | Cl | 552 | $(M + H \text{ of } (Ac)_5\text{-G-AFGP} - AcOH)^+$ |
| + | | 492 | $(M + H \text{ of } (ac)5\text{-G-AFGP} - 2 AcOH)^+$ |
| (Ac)$_2$O | El | 551 | $(M \text{ of } (Ac)_5\text{-G-AFGP} - AcOH)^+$. |
| | Exact Mass | 551.1906 | $C_{26}H_{33}HO_{12}$ |
| G-AFGP + | El | 833 | $(M \text{ of } (TMS)_6\text{-G-AFGP})^{30}$. |
| TMSC) + | | 701 | $(M \text{ of } (TMS)6\text{-G-AFGP} - (HO)CH=CH(OTMS))^+$. |
| per- | El | 887 | $(M \text{ of } (per\text{-}dg\text{-}TMS)_6\text{-G-AFGP})^+$. |
| dg-TMSCl | | 746 | $(M \text{ of } (perdg\text{-}TMS)_6\text{-G-AFGP} - (HO)CH=CH(O\text{-}dg\text{-}TMS))^+$. |
| G-AFGP | FF-11 (+) | 448 | $(M \text{ of } (G\text{-}AFGP + 2H) + 2Ha - H)^+$ |
| + | (−) | 425 | $(M \text{ of } (G\text{-}ADGP + 2H) + Na - H)^-$ |
| NaBH$_4$ | | | |

EXAMPLE 2

The alkylating ability of G-AFGP with proteins and amino acids is examined by incubating poly-L-lysine (PLL; 0.02 mM, Mr=55000) at pH 8.5 (0.5% NH$_4$HCO$_3$) with G-AFGP (2.5 mM). After 12 hours, the fraction of greater than 10,000 MW (Centricon microconcentrator) shows an absorbance at 300 nm. Gel filtration (Sephadex G25) demonstrates that 9% of the total chromophore present is attached to the protein.

Additional experiments show that incubation of G-AFGP with 6-AHA or dimethylamine yields compounds absorbing at 300 nm which are retained by cation exchange resin, indicating incorporation of an amino group which could assume a positive charge.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

What is claimed is:

1. A compound of the formula

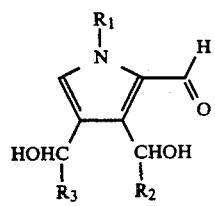

wherein R$_1$ is a des-amino residue of an amino-containing compound; R$_2$ is a glycosyl residue or hydrogen; and R$_3$ is a glycosyl residue.

2. The compound of claim 1, wherein said amino-containing compound is selected from the group consisting of substituted and unsubstituted amino acids, substituted and unsubstituted proteins, and substituted and unsubstituted amino acid-containing biopolymers.

3. The compound of claim 1, wherein said amino-containing compound is selected from the group consisting of 6-aminohexanoic acid, methylamine, poly-L-lysine, alpha-t-BOC-lysine, albumin, collagen, DNA, and glucose residue-bearing compounds where said glucosyl residues are replaced by the residues of another reducing sugar.

4. The compound comprising 1-alkyl-2-formyl-3,4-diglycosyl-pyrroles of the formulae

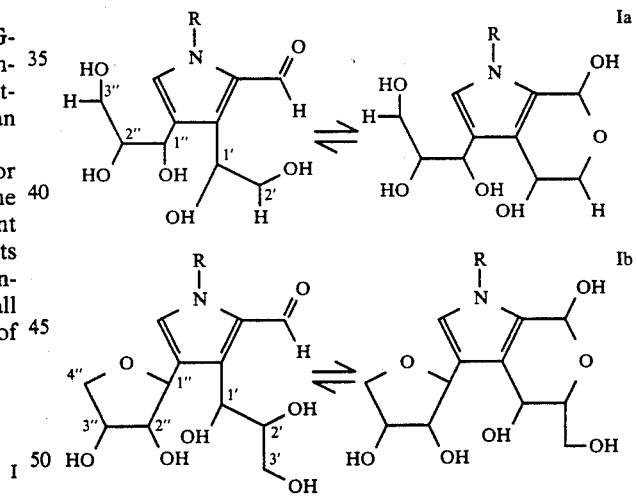

wherein R is a des-amino residue of an amino-containing compound.

5. The compound of claim 4, wherein said amino-containing compound is selected from the group consisting of substituted and unsubstituted amino acids, substituted and unsubstituted proteins, and substituted and unsubstituted amino acid-containing biopolymers.

6. The compound of claim 4, wherein said amino-containing comound is selected from the group consisting of 6-aminohexanoic acid, methylamine, poly-L-lysine, alpha-t-BOC-lysine, albumin, collagin, DNA, and glucose residue-bearing compounds where said glucosyl residues are replaced by the residues of another reducing sugar.

7. The compound of claim 6 wherein said amino-containing compound is derived from poly-L-lysine.

8. A method for the preparation of the chromophore 1-alkyl-2-formyl-3,4-diglycosyl-pyrrole comprising non-enzymatically reacting a carbohydrate selected from the group consisting of glucose and xylose, and an amino-containing compound selected form the group consisting of substituted and unsubstituted amino acids, substituted and unsubstituted proteins, substituted and unsubstituted amino acid-containing biopolymers, and mixtures thereof, in the presence of sulfites.

9. The method of claim 8, wherein said amino-containing compound is selected from the group consisting of 6-aminohexanoic acid, methylamine, poly-L-lysine, alpha-t-BOC-lysine, albumin, collagen, DNA, and glucose residue-bearing compounds where said glucosyl residues are replaced by the residues of another reducing sugar.

10. The method of claim 9, wherein said glucose residue-bearing compounds are selected from the group consisting of proteins, biopolymers, and compounds having the chemical structure equivalent thereto.

* * * * *